United States Patent [19]

Richards et al.

[11] 3,971,073

[45] July 27, 1976

[54] ARTIFICIAL INTRAOCULAR LENS

[75] Inventors: William Richards, Medway; Bernard Grolman, Worcester, both of Mass.

[73] Assignee: American Optical Corporation, Southbridge, Mass.

[22] Filed: Apr. 9, 1975

[21] Appl. No.: 566,468

[52] U.S. Cl. .................................................. 3/13
[51] Int. Cl.² ............................................ A61F 1/16
[58] Field of Search ....................... 3/13, 1; 351/160

[56] References Cited
UNITED STATES PATENTS 3,673,616  7/1972  Fedorov et al. ........................ 3/13

OTHER PUBLICATIONS

"A Weightless Iseikonic Intraocular Lens," by R. D. Binkhorst et al., *American Journal of Ophthalmology*, vol. 58, No. 1, July 1964, pp. 73–78.

"Results of Implantation of Intraocular Lenses in Unilateral Aphakia" by C. D. Binkhorst, American Journal of Ophthalmology, vol. 49, No. 4, Series 3, Apr. 1960, pp. 703–710.

*Primary Examiner*—Ronald L. Frinks
*Attorney, Agent, or Firm*—H. R. Berkenstock, Jr.; William C. Nealon

[57] ABSTRACT

A lens suitable for implantation in the eye is provided with rearwardly disposed laterally extending iris clips anchored inwardly of the lens perimeter within openings extending forwardly into the lens from its rear surface.

10 Claims, 7 Drawing Figures

U.S. Patent   July 27, 1976   3,971,073
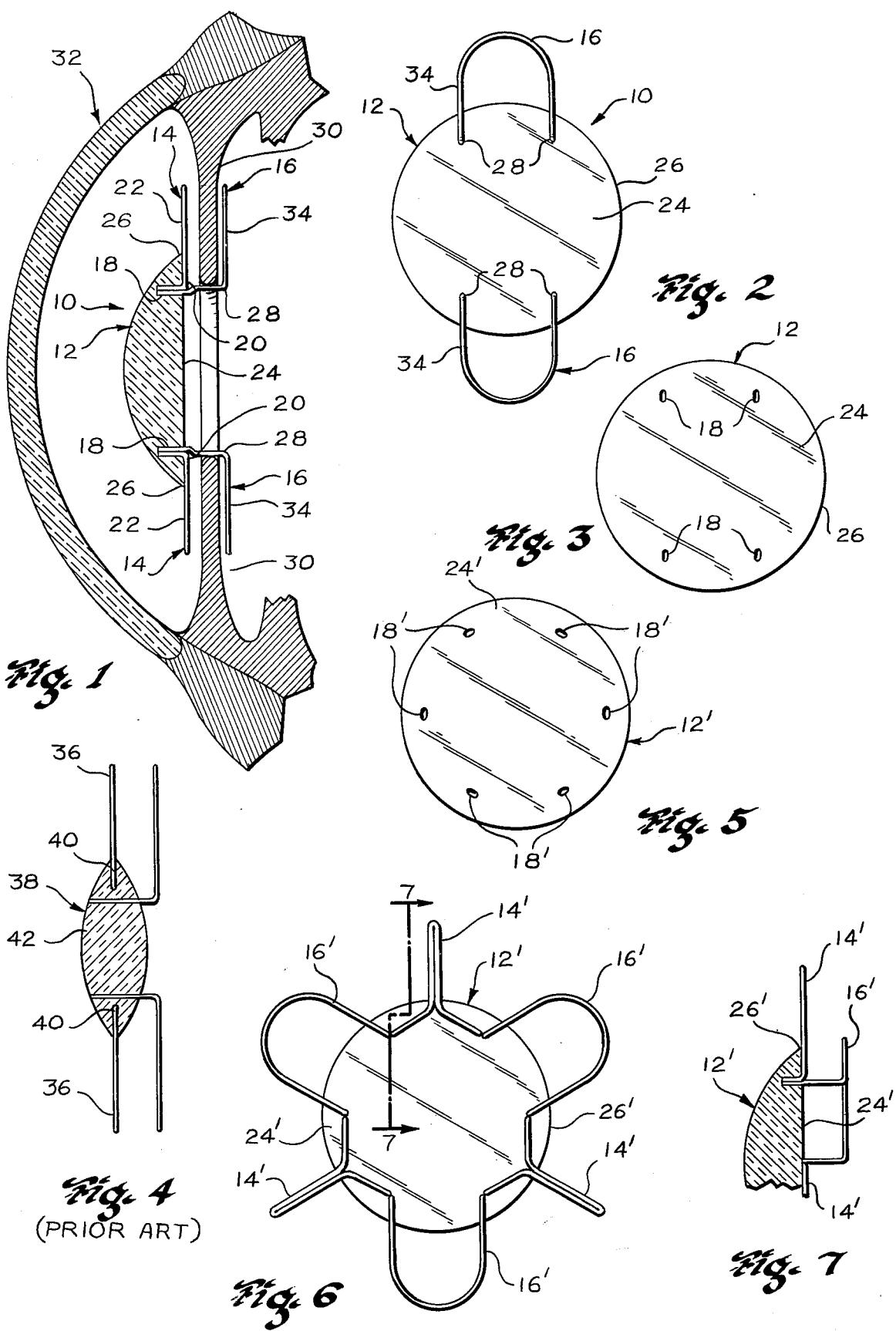

ly parallel to the lens axis. The invention contemplates the use of anchoring holes of the aforesaid type for each anterior and posterior iris clip, which openings may be so shaped and sized as to each accommodate the corresponding one ends of a pair of anterior and posterior iris clips. The thus anchored anterior iris clips are formed, by bending, to follow closely along the posterior side of the lens in the direction of their lateral extensions from respective anchorings. The posterior clips, being somewhat similarly shaped, i.e. by bending, are caused to extend generally parallel to the anterior clips but in rearwardly spaced relationship therewith

ARTIFICIAL INTRAOCULAR LENS

BACKGROUND OF THE INVENTION

1. Field of the Invention

This invention relates to improvements in ophthalmology and more particularly to improvements in artificial intraocular lenses (pseudophakoi) used for the correction of aphakia and re-establishment of binocularity in aphakia.

2. Discussion of the Prior Art

Well-fixed and well-centered intraocular lens implants are known to produce stable retinal images with stable space localization and offer the best chance of re-establishment of binocularity in cases of aphakia.

Many techniques of lens implantation, including suturing to the ciliary muscle as disclosed in U.S. Pat. No. 3,711,870 and iris diaphragm fixation as discussed in U.S. Pat. No. 3,673,616 for example, have been used. The later is considered to be a safe procedure giving good stability and the present invention deals with improvements in this general type of pseudophakos. More particularly, the invention relates to an improved "iris clip" implant having a fastening or haptic section comprised of both posterior and anterior iris clips which are in the form of loops and/or struts of wire or wire-like material.

Hitherto, anchoring of the anterior clips of this type of pseudophakos required the formation of holes in the lens edge which, e.g. by drilling, were extended from the edge into the lens body.

In view of the high plus powers required of artificial intraocular lenses which cause such lenses to ordinarily have thin and/or relatively acute edges, as in U.S. Pat. No. 3,673,616 for example, the forming of anterior clip anchoring holes or openings in the lens edge becomes a delicate and difficult operation to perform successfully. Edge chipping and/or other lens fracturing produce a high scrap yield.

The anchoring of posterior clips, on the otherhand, have not presented the aforesaid problems in that they are normally anchored in holes drilled inwardly of the lens edge and generally parallel to the lens axis.

Accordingly, it is a principal objective of the present invention to overcome the prior art problems and difficulties in anchoring anterior iris clips of pseudophakoi and to thereby provide simple and inexpensive implantable devices of exceptional structural integrity and functional dependability.

SUMMARY OF THE INVENTION

The aforesaid objective and its corollaries are accomplished by uniquely anchoring both the anterior and posterior iris clips of an iris fixation type pseudophakos a substantial distance inwardly of the lens edge within openings extending from the rear surface of the lens toward its opposite front surface, i.e. generally parallel to the lens axis. The invention contemplates the use of anchoring holes of the aforesaid type for each anterior and posterior iris clip, which openings may be so shaped and sized as to each accommodate the corresponding one ends of a pair of anterior and posterior iris clips. The thus anchored anterior iris clips are formed, by bending, to follow closely along the posterior side of the lens in the direction of their lateral extensions from respective anchorings. The posterior clips, being somewhat similarly shaped, i.e. by bending, are caused to extend generally parallel to the anterior clips but in rearwardly spaced relationship therewith for reception of the iris diaphragm. Details of the invention will become more readily apparent from the following description when taken in conjunction with the accompanying drawings.

IN THE DRAWINGS

FIG. 1 is an illustration, in cross-section, of a preferred embodiment of a pseudophakos in situ;

FIG. 2 is a rear elevational view of the pseudophakos;

FIG. 3 is a rear elevational view of the optical section (lens) of the same pseudophakos, its iris clips having been removed for ease and clarity of illustrating certain structural details of the illustrated embodiment of the invention;

FIG. 4 is an illustration, in cross-section, of a prior art pseudophakos wherewith the distinctiveness of the present invention can be more readily understood and appreciated;

FIGS. 5 and 6 are rear elevational views of a modification of the invention; and FIG. 7 is a fragmentary cross-sectional view taken generally along line 7—7 of FIG. 6.

DESCRIPTION OF THE PREFERRED EMBODIMENTS

Referring more particularly to FIGS. 1 and 2 of the drawings, pseudophakos 10 comprises a lens 12 and an array of anterior and posterior iris clips 14 and 16 respectively.

Lens 12 is formed of a material which is biologically inert, i.e. not susceptible to being absorbed by body fluids and capable of being well tolerated by the human body when implanted. Exemplary materials are quartz, ophthalmic glass, methylmethacrylate resins such as those available under the tradenames "Lucite" and "Plexiglass" and biologically neutral, chemically pure polymethylmethacrylates or biologically inert polymeric materials.

Iris clips 14 and 16 are, for similar reasons of avoiding irritation and/or human body rejections of its components, formed of a biologically inert material such as platinum, titanium or an extruded polyamide such as nylon or one or more of the other aforementioned plastic materials.

Iris clips 14, 16 and others to be described hereinafter will be referred to as being "wire" or "formed of wire". It should be understood, however, that the term wire as used in this specification and its appended claims is intended to include strands, strips, rods or fibers of biologically inert material whether the material is metallic or plastic and/or whether one or both is used to make up the array of iris clips.

Lens 12 is provided with four generally oblong openings 18 (FIG. 3) into which ends of iris clips 14 and 16 are extended for anchoring in the lens 12, as best illustrated in FIG. 1. Openings 18 are preferably of a width approximately equal to the wire size of clips 14 and 16 and are of a length approximately equal to twice this dimension. In depth, openings 18 may extend completely through lens 12 or terminate short of the front surface of lens 12 as illustrated in FIG. 1.

The corresponding one ends of a pair of clips 14 and 16 are inserted into each of openings 18 as shown in FIGS. 1 and 2. Anchoring of these ends against accidental withdrawal from openings 18 may be effected by press fittings and/or cementing or fusing the same in place.

Anterior clips 14 which are each in the configuration of a loop similar in appearance to loops 16 (FIG. 2) are provided with a right angular bend 20 directing their loop portions 22 along the rear surface 24 of lens 12 laterally away from edge 26 as shown in FIG. 1.

Posterior iris clips 16 are caused to extend from openings 18 a distance rearwardly of surface 24 of lens 12 sufficiently to provide a bight 28 between corresponding pairs of clips 14 and 16 within which an iris 30 of an eye 32 (FIG. 1) may be received. Between the bights 28 of each clip 16 (FIG. 2), loop portion 34 extends laterally of lens 12, e.g. generally parallel to loops 22 of anterior clips 14. This is produced by right angular bends in the outermost portions of corresponding bights 28.

By comparison of the FIGS. 1 and 2 embodiment of the invention with the FIG. 4 illustration of a prior art structure wherein anterior iris clips 36 of the pseudophakos 38 are anchored in openings 40 formed directly in the edge of lens 42, the improvement of the present invention in overcoming the need for edge drilling can readily be seen. Anterior iris clips 14 of the FIGS. 1 and 2 embodiment of the present invention extend partially along the rear surface 24 of lens 12 from holes 18 in the lens which are located a substantial distance inwardly of the lens edge.

It should be understood that while openings 18 have been showed in preferred form as being oval and dimensioned as stated hereinabove, these openings may each comprise two immediately juxtapositioned drilled or similarly formed circular openings each of a diametral dimension matching the wire sizes of iris clips 14 and 16 to be anchored therein.

It should also be understood that the invention is further adaptable to the use of either larger or smaller wire sizes for posterior iris clips 16 than are used for the anterior clips 14, holes 18 being adjusted accordingly.

While the anterior and posterior clips 14 and 16 have been illustrated as being of substantially equal sizes and parallel to each other in their lateral extensions, they may, if desired, be individually or collectively differently angled relative to each other and/or relative to surface 24 of lens 12, i.e. to suit particular requirements. Lens 12 may also be bi-convex rather than plano-convex, if desired.

Referring more particularly to the modification of the invention illustrated in FIGS. 5, 6 and 7, it can be seen that in this embodiment, six openings 18' each similar to openings 18 of FIG. 3 are provided in the rear surface 24' of lens 12'. In this case, however, each opening 18' receives one end of each of the wires which make up adjoining anterior and posterior iris clips 14' and 16' respectively of the array of clips illustrated in FIG. 6. Anterior iris clips 14' in this embodiment of the invention are formed into strut-like configurations while posterior clips 16' are each in the configuration of a loop. Anterior clips 14' are further so shaped as to follow along the rear surface 24' of lens 12' in their extension laterally away from edge 26' of the lens. Posterior clips 16' extend rearwardly of surface 24' of the lens and thence substantially right angularly in a direction generally parallel to clips 14'. They may be sloped away from the plane of clips 14', if desired. Clips 14' may, alternatively, be in the configuration of loops, e.g. similar to clips 14 of FIG. 1, rather than the strut-like configuration shown. They may also be longer or shorter than clips 16' according to particular use applications and/or preferences of the ophthalmologist.

It is still further contemplated that clips 14 of FIG. 1 and 14' of FIG. 6, being intended for positioning forwardly of the iris in the anterior chamber of an eye, may be formed of a transparent material such as an extruded polyamide, e.g. nylon. Clips 16 (FIG. 1) and 16' (FIG. 6) being intended for positioning in the iridocapsular cleft and accordingly, substantially invisible when the respective pseudophakos is in use, may be formed of a metal such as platinum or titanium. The use of either all metal or all plastic clips 14, 16, 14' and 16' is, of course, contemplated as pointed out hereinabove.

It can be seen from the foregoing description that the prior art practice of drilling or otherwise forming anchoring openings in the edge of an implantable lens for receiving anterior iris clips of a pseudophakos, e.g. as shown in FIG. 4, has been obviated by the present invention. Thus, the hitherto delicate, difficult and costly lens edge drilling operations and their attending problems of lens fracturing, edge chipping and general high scrap yield have been overcome. The present invention provides implantable intraocular devices which are of exceptional structural integrity and functional dependability yet uniquely simple and inexpensive to manufacture.

We claim:
1. A pseudophakos comprising:
   a lens;
   an array of wire anterior and posterior iris clips;
   a number of openings extending into one side of said lens, each located a substantial distance inwardly of the lens edge;
   each anterior iris clip of said array having its opposite ends extended into and anchored within one of a preselected pair of said openings, said anterior clip being bent adjacent said lens surface to extend from said pair of openings laterally of said lens;
   each posterior iris clip of said array having its opposite ends also extended into and anchored within one of a preselected pair of said openings, said posterior clip being further extended a substantial distance away from said side of said lens and thence bent to extend laterally of said lens.

2. A pseudophakos according to claim 1 wherein said openings extending into said one side of said lens are of such precontrolled size and shape as to each relatively intimately receive one end of each of a pair of anterior and posterior iris clips for simultaneous anchoring thereof in said lens.

3. A pseudophakos according to claim 2 wherein one end of each of a pair of anterior and posterior iris clips is extended into and anchored within each of said openings in said lens.

4. A pseudophakos according to claim 3 wherein said openings are disposed successively and substantially equally spaced apart in a circular pattern and said anterior and posterior iris clips are extended alternately from one of said openings to the next adjacent openings in said succession thereof.

5. A pseudophakos according to claim 2 wherein the corresponding opposite ends of each of a pair of anterior and posterior irisclips are anchored in a single pair of said openings of precontrolled size.

6. A pseudophakos according to claim 1 wherein the wire of each anterior and posterior iris clip is formed into the configuration of a loop.

7. A pseudophakos according to claim 1 wherein the wire of each anterior iris clip is formed into the configuration of a strut.

8. A pseudophakos according to claim 1 wherein said anterior iris clips are formed of a plastic material and said posterior iris clips are formed of metal.

9. A pseudophakos according to claim 1 wherein said anterior and posterior iris clips are all formed of a metal.

10. A pseudophakos according to claim 1 wherein said anterior and posterior iris clips are all formed of a plastic material.

* * * * *